(12) United States Patent
Laas et al.

(10) Patent No.: US 7,956,209 B2
(45) Date of Patent: Jun. 7, 2011

(54) POLYISOCYANATES CONTAINING ALLOPHANATE AND SILANE GROUPS

(75) Inventors: Hans-Josef Laas, Odenthal (DE); Reinhard Halpaap, Odenthal (DE)

(73) Assignee: Bayer MaterialScience AG, Leverkusen (DE)

( * ) Notice: Subject to any disclaimer, the term of this patent is extended or adjusted under 35 U.S.C. 154(b) by 314 days.

(21) Appl. No.: 12/171,737

(22) Filed: Jul. 11, 2008

(65) Prior Publication Data

US 2009/0018302 A1    Jan. 15, 2009

(30) Foreign Application Priority Data

Jul. 13, 2007 (DE) .................. 10 2007 032 666

(51) Int. Cl.
*C07F 7/18* (2006.01)
(52) U.S. Cl. ........ 556/413; 556/414; 556/418; 556/419; 556/420; 556/482
(58) Field of Classification Search .................. None
See application file for complete search history.

(56) References Cited

U.S. PATENT DOCUMENTS

| | | | |
|---|---|---|---|
| 3,769,318 A | 10/1973 | Windemuth et al. | |
| 4,104,296 A | 8/1978 | Pike | |
| 4,160,080 A | 7/1979 | Köenig et al. | |
| 4,468,492 A | 8/1984 | Piccirilli et al. | |
| 5,039,385 A * | 8/1991 | Tominaga | 428/418 |
| 5,126,170 A | 6/1992 | Zwiener et al. | |
| 5,252,696 A | 10/1993 | Laas et al. | |
| 5,364,955 A | 11/1994 | Zwiener et al. | |
| 5,587,502 A * | 12/1996 | Moren et al. | 556/420 |
| 5,854,338 A | 12/1998 | Hovestadt et al. | |
| 6,426,414 B1 | 7/2002 | Laas et al. | |
| 6,534,568 B1 * | 3/2003 | Katz et al. | 523/212 |
| 6,767,958 B2 | 7/2004 | Laas et al. | |
| 6,833,423 B2 * | 12/2004 | Roesler et al. | 528/33 |
| 2002/0160199 A1 | 10/2002 | Hofacker et al. | |
| 2003/0027921 A1 | 2/2003 | Speier et al. | |
| 2004/0077778 A1 | 4/2004 | Hazan et al. | |
| 2005/0032974 A1 | 2/2005 | Krebs et al. | |
| 2006/0173140 A1 | 8/2006 | Roesler et al. | |
| 2009/0111938 A1 * | 4/2009 | Hazan | 524/589 |

FOREIGN PATENT DOCUMENTS

| | | |
|---|---|---|
| EP | 0000194 A1 | 1/1979 |
| EP | 0403921 A2 | 12/1990 |
| EP | 0540985 A1 | 5/1993 |
| EP | 0596360 A1 | 5/1994 |
| EP | 0649866 A1 | 4/1995 |
| EP | 0872499 A1 | 10/1998 |
| EP | 0833830 B1 | 3/1999 |
| EP | 0949284 A1 | 10/1999 |
| EP | 0959087 A1 | 11/1999 |
| EP | 0994139 A1 | 4/2000 |
| EP | 1273840 A2 | 1/2003 |
| EP | 1287052 B1 | 8/2004 |
| GB | 994890 A | 6/1965 |
| JP | 2005-15644 A | 1/2005 |
| WO | WO-98/18844 A1 | 5/1998 |
| WO | WO 02/02244 A2 | 1/2002 |
| WO | WO-02/058569 A1 | 8/2002 |
| WO | WO-03/054049 A1 | 7/2003 |
| WO | WO 2004/014991 A1 | 2/2004 |
| WO | WO 2005/066667 A1 | 7/2005 |
| WO | WO 2005/090500 A1 | 9/2005 |

* cited by examiner

*Primary Examiner* — Marc S Zimmer
(74) *Attorney, Agent, or Firm* — Connolly Bove Lodge & Hutz LLP

(57) ABSTRACT

The invention relates to polyisocyanates containing allophanate groups and silane groups, to a process for preparing them and to their use as a starting component in the production of polyurethane polymers, more particularly as a crosslinker component in polyurethane paints and coatings.

17 Claims, No Drawings

POLYISOCYANATES CONTAINING ALLOPHANATE AND SILANE GROUPS

RELATED APPLICATIONS

This application claims benefit to German Patent Application No. 10 2007 032 666.3, filed Jul. 13, 2007, which is incorporated herein by reference in its entirety for all useful purposes.

BACKGROUND OF THE INVENTION

The invention relates to polyisocyanates containing allophanate groups and silane groups, to a process for preparing them and to their use as a starting component in the production of polyurethane polymers, more particularly as a crosslinker component in polyurethane paints and coatings.

Polyisocyanate mixtures containing alkoxysilane groups have been known for some time. Products of this kind, which in addition to the isocyanate group contain a second structure which is reactive, i.e. is capable of crosslinking, have been used in the past in different polyurethane systems and polyurethane applications for the purpose of obtaining specific properties—for example, for enhancing the adhesion, chemical resistance or scratch resistance of coatings.

For example, WO 03/054049 describes isocyanate-functional silanes, prepared from low-monomer-content aliphatic or cycloaliphatic polyisocyanates and secondary aminopropyltrimethoxysilanes, as adhesion promoters for polyurethane hotmelt adhesives.

In accordance with the teaching of JP-A 2005015644, as well, it is possible to enhance the adhesion of adhesives and sealants by using isocyanate prepolymers or polyisocyanates modified with N-substituted, i.e. secondary, aminopropylalkoxysilanes.

EP-B 0 994 139 claims reaction products of aliphatic and/or cycloaliphatic polyisocyanates with deficit amounts of alkoxysilane-functional aspartic esters, of the kind described in EP 0 596 360 as co-reactants for isocyanate-functional compounds, and, if desired, polyethylene oxide polyether alcohols, as binders for one-component moisture-crosslinking coatings, adhesives or sealants featuring accelerated curing.

Reaction products of aliphatic and/or cycloaliphatic polyisocyanates with deficit amounts of alkoxysilane-functional aspartic esters or secondary aminoalkylsilanes are also described in WO 02/058569 as crosslinker components for two-component polyurethane adhesion primers.

EP-B 0 872 499 describes aqueous two-component polyurethane coating materials comprising as their crosslinker component compounds containing isocyanate groups and alkoxysilyl groups. The use of these specific polyisocyanates leads to coatings combining enhanced water resistance with high gloss.

Hydrophilically modified polyisocyanates containing alkoxysilane groups, which are therefore easier to emulsify, have likewise already been identified as crosslinker components for aqueous 2K (2-component) coating and adhesive dispersions (e.g. EP-A 0 949 284).

Recent times have seen the proposal, as a crosslinker component for improving the scratch resistance of solvent-borne, thermosetting, 2K PU automotive clearcoat and topcoat materials, of reaction products of aliphatic and/or cycloaliphatic polyisocyanates with N,N-bis(trialkoxysilylpropyl)amines (PP 1 273 640).

A feature common to all of these polyisocyanate mixtures containing silane groups is that they are prepared by proportional reaction of unmodified polyisocyanates or polyisocyanate prepolymers with organofunctional silanes containing groups that are reactive towards isocyanate groups, examples being mercapto-functional silanes, primary aminoalkylsilanes, secondary N-alkyl-substituted aminoalkylsilanes or alkoxysilane-functional aspartic esters.

Modification of this kind, however, leads inevitably to a reduction in the average isocyanate functionality relative to that of the starting polyisocyanates. The effect of this reduction increases in proportion with the target silane content of the reaction product. In practice, however, in the above mentioned applications, such as coating materials or adhesives, for example, the specific desire, in order to obtain a high network density, is for polyisocyanate crosslinkers having a very high isocyanate functionality.

Moreover, as the degree of modification increases, there is also a drastic rise in the viscosity of the products, owing to the thiourethane groups and, more particularly, urea groups introduced into the molecule; for this reason, the existing polyisocyanates containing silane groups can generally only be employed in dissolved form using considerable quantities of organic solvents.

A further disadvantage of the existing preparation processes for such products is that the reaction of polyisocyanates with isocyanate-reactive organofunctional silanes leads to a random distribution of the silane functions over the oligomeric polyisocyanate mixture. As well as containing the desired silane-functionalized polyisocyanates, the reaction mixture always also includes unmodified starting polyisocyanate and—to an increasing extent with increasing degree of modification—completely isocyanate-free molecules, carrying exclusively silane groups as their reactive groups. When products of this kind are used as crosslinkers in polyurethane systems, the outcome is an inhomogeneous distribution of the silane units in the polymer backbone, and hence not the best-possible level of properties.

EMBODIMENTS OF THE INVENTION

An embodiment of the present invention is a process for preparing polyisocyanates containing allophanate groups comprising reacting A) at least one hydroxyurethane and/or hydroxyamide containing silane groups obtainable from the reaction of aminosilanes with cyclic carbonates and/or lactones with a molar excess amount, based on the NCO-reactive groups of A), of B) at least one diisocyanate having aliphatically, cycloaliphatically, araliphatically, and/or aromatically attached isocyanate groups; and optionally subsequently removing unreacted excess diisocyanate.

Another embodiment of the present invention is the above process, wherein A) comprises a reaction product of aminosilanes of general formula (I)

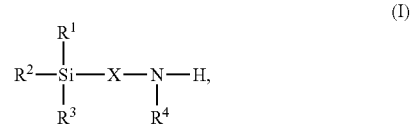

wherein
R$^1$, R$^2$ and R$^3$ are, identically or differently, a saturated or unsaturated, linear or branched, aliphatic or cycloaliphatic, or optionally substituted aromatic or araliphatic radical having up to 18 carbon atoms optionally comprising up to 3 heteroatoms from the series oxygen, sulphur, and nitrogen;

X is a linear or branched organic radical having at least 2 carbon atoms optionally comprising up to 2 imino (—NH—) groups; and $R^4$ is hydrogen, or a saturated or unsaturated, linear or branched, aliphatic or cycloaliphatic, or optionally substituted aromatic or araliphatic radical having up to 18 carbon atoms, or a radical of formula

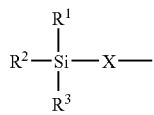

wherein $R^1$, $R^2$, $R^3$, and X are as defined above,
with cyclic carbonates and/or lactones.

Another embodiment of the present invention is the above process, wherein A) comprises a reaction product of aminosilanes of general formula (I)

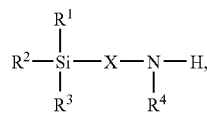

wherein $R^1$, $R^2$ and $R^3$ are, identically or differently, a saturated, linear or branched, aliphatic or cycloaliphatic radical having up to 6 carbon atoms optionally comprising up to 3 oxygen atoms;

X is a linear or branched alkylene radical having 2 to 10 carbon atoms optionally comprising up to 2 (—NH—) imino groups; and $R^4$ is hydrogen, a saturated, linear or branched, aliphatic or cycloaliphatic radical having up to 6 carbon atoms, or a radical of formula

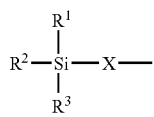

wherein $R^1$, $R^2$, $R^3$, and X are as defined above,
with cyclic carbonates and/or lactones.

Another embodiment of the present invention is the above process, wherein A) comprises a reaction product of aminosilanes of the general formula (I)

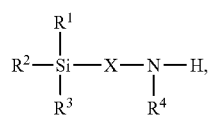

wherein $R^1$, $R^2$ and $R^3$ are each alkyl radicals having up to 6 carbon atoms and/or alkoxy radicals which contain up to 3 oxygen atoms, with the proviso that at least one of $R^1$, $R^2$ and $R^3$ is an alkoxy radical;

X is a linear or branched alkylene radical having 3 or 4 carbon atoms; and $R^4$ is hydrogen, a methyl radical, or a radical of the formula

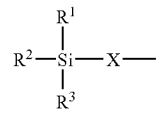

wherein $R^1$, $R^2$, $R^3$, and X are as defined above,
with cyclic carbonates and/or lactones.

Another embodiment of the present invention is the above process, wherein A) comprises a reaction product of aminosilanes of the general formula (I)

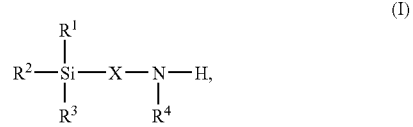

wherein
$R^1$, $R^2$ and $R^3$ are, identically or differently methyl, methoxy, or ethoxy radical, with the proviso that at least one of $R^1$, $R^2$ and $R^3$ is a methoxy or ethoxy radical;
X is a propylene (—$CH_2$—$CH_2$—$CH_2$—) radical; and
$R^4$ is hydrogen, a methyl radical, or a radical of formula

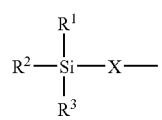

wherein $R^1$, $R^2$, $R^3$, and X are as defined above,
with cyclic carbonates and/or lactones.

Another embodiment of the present invention is the above process, wherein A) comprises reaction products of 3-aminopropyltrimethoxysilane, 3-aminopropyltriethoxysilane, 3-aminopropylmethyldimethoxysilane, and/or 3-aminopropylmethyldiethoxysilane with cyclic carbonates and/or lactones.

Another embodiment of the present invention is the above process, wherein A) comprises reaction products of aminosilanes with ethylene carbonate and/or propylene carbonate.

Another embodiment of the present invention is the above process, wherein A) comprises reaction products of aminosilanes with β-propiolactone, γ-butyrolactone, γ-valerolactone, γ-caprolactone, and/or ε-caprolactone.

Another embodiment of the present invention is the above process, wherein B) comprises diisocyanates having aliphatically and/or cycloaliphatically attached isocyanate groups.

Another embodiment of the present invention is the above process, wherein B) comprises 1,6-diisocyanatohexane, 1-isocyanato-3,3,5-trimethyl-5-isocyanatomethylcyclohexane, 2,4'- and/or 4,4'-diisocyanatodicyclohexylmethane, or mixtures thereof.

Another embodiment of the present invention is the above process, wherein the reaction is carried out in the presence of a catalyst which accelerates the formation of allophanate groups.

Another embodiment of the present invention is the above process, wherein said catalyst comprises zinc carboxylates and/or zirconium carboxylates.

Another embodiment of the present invention is the above process, wherein said catalyst comprises zinc(II) n-octanoate, zinc(II) 2-ethyl-1-hexanoate, zinc(II) stearate, zirconium(IV) n-octanoate, zirconium(IV) 2-ethyl-1-hexanoate, and/or zirconium(IV) neodecanoate.

Yet another embodiment of the present invention is a polyisocyanate containing allophanate groups prepared by the above process.

Yet another embodiment of the present invention is the above polyisocyanate containing allophanate groups prepared by the above process, wherein said polyisocyanate containing allophanate groups is blocked with blocking agents.

Yet another embodiment of the present invention is a coating composition comprising the polyisocyanate carrying allophanate groups prepared by the above process.

Yet another embodiment of the present invention is a substrate coated with the above coating composition comprising the polyisocyanate carrying allophanate groups prepared by the above process.

DESCRIPTION OF THE INVENTION

It was an object of the present invention, therefore, to provide new polyisocyanates, containing silane groups, that are not hampered by the disadvantages of the prior art. These new polyisocyanates ought to carry both functionalities, i.e. isocyanate groups and silane groups, in every molecule, ought at the same time to have high average isocyanate functionalities, and ought nevertheless to exhibit low viscosities.

This object has been achieved with the provision of the inventively modified polyisocyanates described in more detail below and, respectively, by the process for their preparation.

The present invention is based on the surprising observation that hydroxyurethanes and/or hydroxyamides containing silane groups, obtainable through reaction of aminoalkylsilanes with cyclic carbonates or lactones, with ring opening, can be reacted easily with excess amounts of monomeric diisocyanates to form storage-stable, light-coloured allophanate polyisocyanates which are distinguished by low viscosities even with high isocyanate functionalities and high silane contents.

The present invention provides a process for preparing polyisocyanates containing allophanate groups by reacting A) at least one hydroxyurethane and/or hydroxyamide containing silane groups—obtainable from the reaction of aminosilanes with cyclic carbonates and/or lactones with a molar excess amount, based on the NCO-reactive groups of component A), of B) at least one diisocyanate having aliphatically, cycloaliphatically, araliphatically and/or aromatically attached isocyanate groups and, if desired, subsequently removing the unreacted diisocyanate excess The invention also provides the polyisocyanates containing allophanate groups and silane groups that are obtainable by this process, and further provides for their use as starting components in the production of polyurethane polymers, more particularly as a crosslinker component in polyurethane paints and coatings.

Starting compounds A) for the process of the invention are any desired reaction products of aminosilanes with cyclic carbonates or lactones.

Suitable aminosilanes for preparing the starting compounds A) are, for example, those of the general formula (I)

$$R^2-\underset{\underset{R^3}{|}}{\overset{\overset{R^1}{|}}{Si}}-X-\underset{\underset{R^4}{|}}{N}-H, \quad (I)$$

in which

R$^1$, R$^2$ and R$^3$ are identical or different radicals and are each a saturated or unsaturated, linear or branched, aliphatic or cycloaliphatic, or an optionally substituted aromatic or araliphatic, radical having up to 18 carbon atoms and being able to contain, if desired, up to 3 heteroatoms from the series oxygen, sulphur, nitrogen, X is a linear or branched organic radical having at least 2 carbon atoms and able to contain, if desired, up to 2 imino groups (—NH—), and R$^4$ is hydrogen, a saturated or unsaturated, linear or branched, aliphatic or cycloaliphatic, or an optionally substituted aromatic or araliphatic radical having up to 18 carbon atoms, or a radical of the formula $$R^2-\underset{\underset{R^3}{|}}{\overset{\overset{R^1}{|}}{Si}}-X-$$

in which R$^1$, R$^2$, R$^3$ and X have the definition stated above.

Suitable aminosilanes are, for example, 3-aminopropyltrimethoxysilane, 3-aminopropyl-triethoxysilane, 3-aminopropylmethyldimethoxysilane, 3-aminopropylmethyldiethoxysilane, 3-aminopropylethyldiethoxysilane, 3-aminopropyldimethylethoxysilane, 3-aminopropyldiisopropylethoxysilane, 3-aminopropyltripropoxysilane, 3-aminopropyltributoxysilane, 3-aminopropylphenyldiethoxysilane, 3-aminopropylphenyldimethoxysilane, 3-aminopropyltris(methoxyethoxyethoxy)silane, 2-aminoisopropyltrimethoxysilane, 4-aminobutyltrimethoxysilane, 4-aminobutyltriethoxysilane, 4-aminobutylmethyldimethoxysilane, 4-aminobutylmethyldiethoxysilane, 4-aminobutylethyldimethoxysilane, 4-aminobutylethyldiethoxysilane, 4-aminobutyldimethylmethoxysilane, 4-aminobutylphenyldimethoxysilane, 4-amino-butylphenyldiethoxysilane, 4-amino(3-methylbutyl)methyldimethoxysilane, 4-amino(3-methylbutyl)methyldiethoxysilane, 4-amino(3-methylbutyl)trimethoxysilane, 3-aminopropylphenylmethyl-n-propoxysilane, 3-aminopropylmethyldibutoxysilane, 3-aminopropyldiethylmethylsilane, 3-aminopropylmethylbis(trimethylsiloxy)silane, 11-aminoundecyltrimethoxysilane, N-methyl-3-aminopropyltriethoxysilane, N-(n-butyl)-3-aminopropyltrimethoxysilane, N-(2-aminoethyl)-3-aminopropyltrimethoxysilane, N-(2-aminoethyl)-3-aminoisobutylmethyldimethoxysilane, N-(2-aminoethyl)-3-aminopropylmethyldimethoxysilane, N-(2-aminoethyl)-3-aminopropyltris(2-ethylhexoxy)silane, N-(6-aminohexyl)-3-aminopropyltrimethoxysilane, N-benzyl-N-(2-aminoethyl)-3-aminopropyltrimethoxysilane, bis(3-trimethoxysilylpropyl)amine, bis(3-triethoxysilylpropyl)amine, (aminoethylaminomethyl)phenethyltrimethoxysilane, N-vinylbenzyl-N-(2-aminoethyl)-3-aminopropylpolysiloxane, N-vinylbenzyl-N-(2-aminoethyl)-3-aminopropylpolysiloxane, 3-ureidopropyltriethoxysilane, 3-(m-amino-phenoxy)propyltrimethoxysilane, m- and/or p-aminophenyltrimethoxysilane, 3-(3-aminopropoxy)-3,3-dimethyl-1-propenyltrimethoxysilane, 3-aminopropylmethylbis(trimethylsiloxy)silane, 3-aminopropyltris(trimethylsiloxy)silane, 3-aminopropylpentamethyldisiloxane or any desired mixtures of such aminosilanes.

Preferred aminosilanes for preparing the starting component A) are those of the general formula (I) in which
$R^1$, $R^2$ and $R^3$ are identical or different radicals and are each a saturated, linear or branched, aliphatic or cycloaliphatic radical having up to 6 carbon atoms and able to contain, if desired, up to 3 oxygen atoms,
X is a linear or branched alkylene radical having 2 to 10 carbon atoms and able to contain, if desired, up to 2 imino groups (—NH—),
and
$R^4$ is hydrogen, a saturated, linear or branched, aliphatic or cycloaliphatic radical having up to 6 carbon atoms, or a radical of the formula

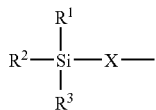

in which $R^1$, $R^2$, $R^3$ and X have the definition stated above.
Preferably
$R^1$, $R^2$ and $R^3$ are each alkyl radicals having up to 6 carbon atoms and/or alkoxy radicals which contain up to 3 oxygen atoms, with the proviso that at least one of the radicals $R^1$, $R^2$ and $R^3$ is such an alkoxy radical,
X is a linear or branched alkylene radical having 3 or 4 carbon atoms, and
$R^4$ is hydrogen, a methyl radical or a radical of the formula

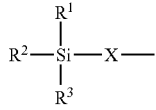

in which $R^1$, $R^2$, $R^3$ and X have the definition stated above.
With particular preference
$R^1$, $R^2$ and $R^3$ are each methyl, methoxy and/or ethoxy, with the proviso that at least one of the radicals $R^1$, $R^2$ and $R^3$ is a methoxy or ethoxy radical,
X is a propylene radical (—$CH_2$—$CH_2$—$CH_2$—), and
$R^4$ is hydrogen, a methyl radical or a radical of the formula

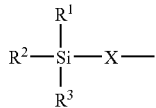

in which $R^1$, $R^2$, $R^3$ and X have the definition stated above.

Particularly preferred aminosilanes are 3-aminopropyltrimethoxysilane, 3-aminopropyl-triethoxysilane, 3-amninopropylmethyldimethoxysilane and/or 3-aminopropylmethyldiethoxysilane.

In the preparation of the starting compounds A) for the process of the invention the stated amino silanes are reacted with any desired cyclic carbonates and/or lactones with ring opening.

Suitable cyclic carbonates are more particularly those having 3 or 4 carbon atoms in the ring, and if desired may also be substituted, such as, for example, 1,3-dioxolan-2-one (ethylene carbonate, EC), 4-chloro-1,3-dioxolan-2-one, 4,5-dichloro-1,3-dioxolan-2-one, 4-methyl-1,3-dioxolan-2-one (propylene carbonate, PC), 4-ethyl-1,3-dioxolan-2-one, 4,5-dimethyl-1,3-dioxolan-2-one, 4,4-dimethyl-1,3-dioxolan-2-one, 4-hydroxymethyl-1,3-dioxolan-2-one (glycerol carbonate), 4-phenoxymethyl-1,3-dioxolan-2-one, 1,3-dioxan-2-one (trimethylene carbonate), 5,5-dimethyl-1,3-dioxan-2-one, 5-methyl-5-propyl-1,3-dioxan-2-one, 5-ethyl-5-(hydroxymethyl)-1,3-dioxan-2-one (TMP carbonate), 4-isopropyl-5,5-dimethyl-1,3-dioxan-2-one (2,2,4-trimethylpentane-1,3-diol carbonate), 4-tert-butyl-5-methyl-1,3-dioxan-2-one (2,4,4-trimethylpentane-1,3-diol carbonate), 2,4-dioxaspiro[5.5]undecan-3-one (cyclohexane-1,1-dimethanol spirocarbonate) or any desired mixtures of such cyclic carbonates. Preferred cyclic carbonates are ethylene carbonate and/or propylene carbonate.

Suitable lactones are, for example, those having 3 to 6 carbon atoms in the ring, and if desire may also be substituted, such as, for example, β-propiolactone, β-butyrolactone, β-butyrolactone, α-methyl-γ-butyrolactone, γ-valerolactone, γ-phenyl-γ-butyrolactone, α,α-diphenyl-γ-butyrolactone, γ-hexalactone(γ-caprolactone), γ-heptalactone, γ-octalactone, γ-nonalactone, γ-decalactone, γ-undecalactone, γ-dodecalactone, γ-methyl-γ-decanolactone, α-acetyl-γ-butyrolactone, δ-valerolactone, δ-hexanolactone, δ-octanolactone, δ-nonanolactone, δ-decalactone, δ-undecalactone, δ-tridecalactone, δ-tetradecalactone, γ-ethyl-γ-butyl-δ-valerolactone, octahydrocoumarin, ε-caprolactone, γ-phenyl-ε-caprolactone, ε-decalactone or any desired mixtures of such lactones. Preferred lactones are β-propiolactone, γ-butyrolactone, γ-valerolactone, γ-caprolactone and/or ε-caprolactone.

The preparation of the starting compounds A) by reaction of the stated aminosilanes with the cyclic carbonates or lactones is known per se and can take place, for example, in accordance with the processes described in SU 295764, U.S. Pat. No. 4,104,296, EP-B 0 833 830 or WO 98/18844. In these cases, generally, the reactants are reacted with one another in equimolar amounts at temperatures of 15 to 100° C., preferably 20 to 60° C. An alternative option is to use one of the components, for example the aminosilane or the cyclic carbonate and/or lactone, in a molar excess amount, but preferably in an excess of not more than 10 mol %, with particular preference of not more than 5 mol %. The hydroxy-functional starting compounds A) obtainable in this way, which when cyclic carbonates are used contain urethane groups and when lactones are used contain amide groups, are, in general, colourless liquids of low viscosity.

Suitable starting compounds B) for the process of the invention are any desired diisocyanates having aliphatically, cycloaliphatically, araliphatically and/or aromatically attached isocyanate groups, which may have been prepared by any desired processes, for example by phosgenation or by a phosgene-free route, for example by urethane cleavage. Examples of suitable starting diisocyanates are those of the molecular weight range 140 to 400 g/mol, such as 1,4-diisocyanatobutane, 1,6-diisocyanatohexane (HDI), 1,5-diisocyanato-2,2-dimethylpentane, 2,2,4- or 2,4,4-trimethyl-1,6-diisocyanatohexane, 1,10-diisocyanatodecane, 1,3- and 1,4-diisocyanatocyclohexane, 1,4-diisocyanato-3,3,5-trimethylcyclohexane, 1,3-diisocyanato-2-methylcyclohexane, 1,3-diisocyanato-4-methylcyclohexane, 1-isocyanato-3,3,5-trimethyl-5-isocyanatomethylcyclohexane (isophorone diisocyanate; IPDI), 1-isocyanato-1-methyl-4(3)-isocyanatomethylcyclohexane, 2,4'- and 4,4'-diisocyanatodicyclohexylmethane, 1,3- and 1,4-bis(isocyanatomethyl)cyclohexane, 4,4'-diisocyanato-3,3'-dimethyldicyclohexylmethane, 4,4'-diisocyanato-3,3',5,5'-tetramethyldicyclohexylmethane, 4,4'-diisocyanato-1,1'-bi(cyclohexyl), 4,4'-diisocyanato-3,3'-dimethyl-1,1'-bi(cyclohexyl), 4,4'-diisocyanato-2,2',5,5'-tetramethyl-1,1'-bi(cyclohexyl), 1,8-diisocyanato-p-menthane, 1,3-diisocyanatoadamantane, 1,3-dimethyl-5,7-diisocyanatoadamantane, 1,3- and 1,4-bis(isocyanatomethyl)benzene, 1,3- and 1,4-bis(1-isocyanato-1-methylethyl)benzene (TMXDI), bis(4-(1-isocyanato-1-methylethyl)phenyl)carbonate, 1,3- and 1,4-phenylene diisocyanate, 2,4- and 2,6-tolylene diisocyanate, and any desired mixtures of these isomers, diphenylmethane 2,4'- and/or 4,4'-diisocyanate and naphthylene 1,5-diisocyanate, and any desired mixtures of such diisocyanates. Further duisocyanates likewise suitable are found, furthermore, for example, in Justus Liebigs Annalen der Chemie volume 562 (1949) pp. 75-136.

Preferred as starting component B) are the stated diisocyanates having aliphatically and/or cycloaliphatically attached isocyanate groups.

Particularly preferred starting components B) for the process of the invention are 1,6-diisocyanatohexane, 1-isocyanato-3,3,5-trimethyl-5-isocyanatomethylcyclohexane, 2,4'- and/or 4,4'-diisocyanatodicyclohexylmethane or any desired mixtures of these diisocyanates.

To carry out the process of the invention, the hydroxyamides and/or hydroxyurethanes A) containing silane groups are reacted with the diisocyanates B) at temperatures of 40 to 200° C., preferably 60 to 180° C., observing an equivalent ratio of isocyanate groups to isocyanate-reactive groups of 4:1 to 50:1, preferably of 5:1 to 30:1, to give allophanate polyisocyanates.

"Isocyanate-reactive groups" for the purposes of the present invention include not only the hydroxyl groups of component A) and the urethane groups which form from them as an intermediate product through NCO/OH reaction, but also, when using hydroxy urethanes, the urethane groups already present therein, since under the reaction conditions these urethane groups likewise react further to form allophanate groups.

The process of the invention can be carried out without catalysis, as a thermally induced allophanatization. Preferably, however, suitable catalysts are used in order to accelerate the allophanatization reaction. These catalysts are the typical, known allophanatization catalysts, examples being metal carboxylates, metal chelates or tertiary amines of the type described in GB-A-0 994 890, alkylating agents of the type described in U.S. Pat. No. 3,769,318, or strong acids, as described by way of example in EP-A-0 000 194.

Suitable allophanatization catalysts are more particularly zinc compounds, such as zinc(II) stearate, zinc(II) n-octanoate, zinc(II) 2-ethyl-1-hexanoate, zinc(II) naphthenate or zinc(II) acetylacetonate, tin compounds, such as tin(II) n-octanoate, tin(II) 2-ethyl-1-hexanoate, tin(II) laurate, dibutyltin oxide, dibutyltin dichloride, dibutyltin diacetate, dibutyltin dilaurate, dibutyltin dimaleate or dioctyltin diacetate, zirconium compounds, such as zirconium(IV) 2-ethyl-1-hexanoate, zirconium(IV) neodecanoate, zirconium(IV) naphthenate or zirconium(IV) acetylacetonate, aluminium tri(ethyl acetoacetate), iron(III) chloride, potassium octoate, manganese compounds, cobalt compounds or nickel compounds, and also strong acids, such as trifluoroacetic acid sulphuric acid, hydrochloric acid, hydrobromic acid, phosphoric acid or perchloric acid, or any desired mixtures of these catalysts.

Also suitable, albeit less preferred, catalysts for the process of the invention are compounds which as well as the allophanatization reaction also catalyse the trimerization of isocyanate groups to form isocyanurate structures. Catalysts of this kind are described for example in EP-A-0 649 866 page 4, line 7 to page 5 line 15.

Preferred catalysts for the process of the invention are zinc compounds and/or zirconium compounds of the aforementioned kind Very particular preference is given to using zinc (II) n-octanoate, zinc(II) 2-ethyl-1-hexanoate and/or zinc(II) stearate, zirconium(IV) n-octanoate, zirconium(IV) 2-ethyl-1-hexanoate and/or zirconium (IV) neodecanoate.

In the process of the invention these catalysts are employed, if at all, in an amount of 0.001% to 5% by weight, preferably 0.005% to 1% by weight, based on the total weight of the reactants A) and B), and can be added both before the commencement of reaction and at any point in time during the reaction.

The process of the invention is preferably carried out solventlessly. If desired, however, it is also possible to use suitable solvents that are inert towards the reactive groups of the starting components. Examples of suitable solvents are the conventional, typical paint solvents, such as ethyl acetate, butyl acetate, ethylene glycol monomethyl or monoethyl ether acetate, 1-methoxyprop-2-yl acetate, 3-methoxy-n-butyl acetate, acetone, 2-butanone, 4-methyl-2-pentanone, cyclohexanone, toluene, xylene, chlorobenzene, white spirit, aromatics with relatively high degrees of substitution, such as those in commerce, for example, under the names solvent naphtha, Solvesso®, Isopar®, Nappar® (Deutsche EXXON CHEMICAL GmbH, Cologne, Del.) and Shellsol® (Deutsche Shell Chemie GmbH, Eschborn, Del.), but also solvents such as propylene glycol diacetate, diethylene glycol dimethyl ether, dipropylene glycol dimethyl ether, diethylene glycol ethyl and butyl ether acetate, N-methylpyrrolidone and N-methylcaprolactam, or any desired mixtures of such solvents.

In one possible embodiment in the process of the invention the starting diisocyanate B) or a mixture of different starting diisocyanates is charged to the reaction vessel, under inert gas where appropriate, such as under nitrogen, for example, and where appropriate in the presence of a suitable solvent of the type stated, at a temperature between 20 and 100° C. Subsequently, the hydroxyl-functional starting compound A) is added in the amounts stated above and the reaction temperature for the urethanization is set by means where appropriate of a suitable measure (heating or cooling) at a temperature of 30 to 120° C., preferably of 50 to 100° C. Following the urethanization reaction, i.e. when the NCO content corresponding theoretically to complete conversion of isocyanate groups and hydroxyl groups has been reached, the allophanatization can be initiated, for example, without addition of a catalyst, by heating of the reaction mixture to a temperature of 140 to 200° C. To accelerate the allophanatization reaction it is preferred, however, to use suitable catalysts of the aforementioned kind, with temperatures in the range from 60 to 140° C., preferably 80 to 120° C., being sufficient, depending on the nature and amount of the catalyst used.

In another possible embodiment of the process of the invention the catalyst for use where appropriate is mixed in either to the silane component A) and/or to the diisocyanate component B) before the beginning of the actual reaction. In this case the urethane groups which form as an intermediate product and, if using hydroxy urethanes A), are already contained in the latter undergo spontaneous further reaction to give the desired allophanate structure. In this kind of one-stage reaction regime, the starting diisocyanates B), which if appropriate contain the catalyst, are charged to the reaction vessel, where appropriate under inert gas, such as under nitrogen, for example, and where appropriate in the presence of a suitable solvent of the stated type, generally at temperatures optimum for the allophanatization, in the range from 60 to 140° C., preferably 80 to 120° C., and are reacted with the silane component A), where appropriate containing the catalyst.

A further possibility, however, is to add the catalyst to the reaction mixture at any point in time during the urethanization reaction. With this embodiment of the process of the invention a temperature in the range from 30 to 120° C., preferably from 50 to 100° C., is generally set for the pure urethanization reaction that proceeds before the addition of catalyst. Following addition of a suitable catalyst, the allophanatization reaction is carried out, finally, at temperatures of 60 to 140° C., preferably of 80 to 120° C.

The course of the reaction in the process of the invention can be followed by means, for example, of titrimetric determination of the NCO content. When the target NCO content has been attained, preferably when the degree of allophanatization (i.e. the percentage—calculable from the NCO content—of the urethane groups which have undergone reaction to form allophanate groups, which form as an intermediate product from the hydroxyl groups of component A) and also the urethane groups already present in hydroxy urethanes A) when the latter are employed) of the reaction mixture is at least 80%, with particular preference at least 90%, with very particular preference after complete allophanatization, the reaction is discontinued. In the case of a purely thermal reaction regime, this can be done, for example, by cooling the reaction mixture to room temperature. In the case of the preferred use of an allophanatization catalyst of the stated type, however, the reaction is generally stopped by adding suitable catalyst poisons, examples being acid chlorides such as benzoyl chloride or isophthaloyl dichloride.

Subsequently with preference the reaction mixture is freed by thin-film distillation under a high vacuum, for example under a pressure of below 1.0 mbar, preferably below 0.5 mbar, more preferably below 0.2 mbar, under extremely gentle conditions, for example at a temperature of 100 to 200° C., preferably of 120 to 180° C., from volatile constituents (excess monomeric diisocyanates, cyclic carbonates or lactones used in excess, where appropriate, in the preparation of the starting compounds A), any solvents used and, when no catalyst poison is employed, any active catalyst).

The distillates obtained, which as well as the unreacted monomeric starting diisocyanates contain any cyclic carbonates or lactones used in excess, and any solvent used, and any active catalyst when no catalyst poison is employed, can be used without problems for renewed oligomerization.

In a further embodiment of the process of the invention the stated volatile constituents are separated off from the oligomerization product by extraction with suitable solvents that are inert towards isocyanate groups, examples being aliphatic or cycloaliphatic hydrocarbons such as pentane, hexane, heptane, cyclopentane or cyclohexane.

Independently of the nature of the work-up the products of the process of the invention are clear, light-coloured polyisocyanates which generally have colour numbers of below 200 APHA, preferably of below 100 APHA, more preferably of below 80 APHA, an average NCO functionality of 2.0 to 5.0, preferably 2.4 to 4.8, more preferably 3.0 to 4.5, and an NCO content of 6.0% to 20.5%, preferably 10.0% to 18.0%, more preferably 12.0% to 17.0% by weight. When selective allophanatization catalysts are used the products are virtually free from by-products such as isocyanurates, for example; in other words, in virtually every molecule, there are not only isocyanate functions but also at least one silane group.

The allophanate polyisocyanates of the invention constitute valuable starting materials for producing polyurethane polymers by the isocyanate polyaddition process.

On account of their low viscosity as compared with prior-art silane-modified polyisocyanates they can be used solventlessly, but if needed can also be diluted with typical solvents, examples being the inert paint solvents specified above that may be used where appropriate in the process of the invention, such dilution taking place without clouding.

The silane-modified allophanate polyisocyanates of the invention are outstandingly suitable as curing agents for two-component polyurethane coating materials in which, as polyhydroxyl compounds, the typical polyetherpolyols, polyesterpolyols, polycarbonatepolyols and/or polyacrylatepolyols are present as co-reactants for the polyisocyanates. Particularly preferred co-reactants for the process products of the invention are polyacrylates containing hydroxyl groups, i.e. polymers or copolymers of (meth)acrylic acid alkyl esters, where appropriate with styrene or other copolymerizable olefinically unsaturated monomers.

In general the coating materials formulated with the silane-modified allophanate polyisocyanates of the invention, into which, where appropriate, the auxiliaries and adjuvants typical in the coatings sector may have been incorporated, such as flow control assistants, colour pigments, fillers or matting agents, for example, have good coating properties even on room temperature drying. As will be appreciated, however, they can also be dried under forced conditions at elevated temperature or by baking at temperatures up to 260° C.

In order to control the rate of cure it is possible when formulating the coating compositions to use suitable catalysts, examples being the catalysts typical in isocyanate chemistry, such as tertiary amines, for example, such as triethylamine, pyridine, methylpyridine, benzyldimethylamine, N,N-endoethylenepiperazine, N-methylpiperidine, pentamethyldiethylenetriamine, N,N-dimethylaminocyclohexane, N,N'-dimethylpiperazine or metal salts such as iron(III) chloride, zinc chloride, zinc 2-ethylcaproate, tin(II) octanoate, tin(II) ethylcaproate, dibutyltin(IV) dilaurate, bismuth(III) 2-ethylhexanoate, bismuth(III) octoate or molybdenum glycolate. Also used, in addition, are catalysts which accelerate the hydrolysis and condensation of alkoxysilane groups or their reaction with the hydroxyl groups of the polyol components used as binders. Examples of catalysts of this kind, in addition to above mentioned isocyanate catalysts, are acids, such as p-toluene sulphonic acid, trifluoromethane sulphonic acid, acetic acid, trifluoroacetic acid and dibutyl phosphate, bases, such as N-substituted amidines such as 1,5-diazabicyclo[4.3.0]non-5-ene (DBN) and 1,5-diazabicyclo[5.4.0]undec-7-ene (DBU), but also metal salts or organometallic compounds, such as tetraisopropyl titanate, tetrabutyl titanate, titanium(IV) acetylacetonate, aluminium acetylacetonate, aluminium triflate or tin triflate.

It will be appreciated that the silane-modified allophanate polyisocyanates of the invention can also be used in a form in which they have been blocked with blocking agents known per se from polyurethane chemistry, in combination with the above mentioned film-forming binders or film-forming binder components, as one-component PU baking systems. Examples of suitable blocking agents are diethyl malonate, acetoacetic esters, activated cyclic ketones, such as cyclopentanone 2-carboxymethyl ester and 2-carboxyethyl ester, acetone oxime, butanone oxime, s-caprolactam, 3,5-dimethylpyrazole, 1,2,4-triazole, dimethyl-1,2,4-triazole, imidazole, benzyl-tert-butylamine or any desired mixtures of these blocking agents.

The invention also provides, accordingly, for the use of the polyisocyanates of the invention containing allophanate groups for preparing polyisocyanates blocked with blocking agents known from polyurethane chemistry, and also provides the resultant blocked polyisocyanates themselves.

The process products of the invention can also be combined with polyamines, such as with the polyaspartic acid derivatives known from EP-B 0 403 921, or else with polyamines whose amino groups are in blocked form, such as polyketimines, polyaldimines or oxazolanes. Under the influence of moisture, these blocked amino groups produce free amino groups and, in the case of the oxazolanes, free hydroxyl groups as well, which are consumed by reaction with the isocyanate groups of the silane-modified allophanate polyisocyanates and in the course of such reaction effect crosslinking.

The silane-modified allophanate polyisocyanates of the invention are also suitable as crosslinker components for binders or binder components that are present in solution or dispersion in water and have isocyanate-reactive groups, more particularly alcoholic hydroxyl groups, in the case of the preparation of aqueous two-component polyurethane systems. On account of their low viscosity they can be used either as they are, i.e. in hydrophobic form, or else in a form in which they have been hydrophilically modified by known processes, in accordance for example with EP-B 0 540 985, EP-B 0 959 087 or EP-B 1 287 052.

Where appropriate, the coating systems formulated with the silane-modified allophanate polyisocyanates of the invention may also be admixed with any desired further hydrolysable silane compounds, such as tetramethoxysilane, tetraethoxysilane, methyltrimethoxysilane, methyltriethoxysilane, ethyltriethoxysilane, isobutyltrimethoxysilane, isobutyltriethoxysilane, octyltriethoxysilane, octyltrimethoxysilane, (3-glycidyloxypropyl)methyldiethoxysilane, (3-glycidyloxypropyl)trimethoxysilane, phenyltrimethoxysilane or phenyltriethoxysilane, or mixtures of such silane compounds, as co-reactants.

In all coating material combinations, the process products of the invention and the co-reactant are in amounts such that for each unblocked or blocked isocyanate group there are 0.5 to 3, preferably 0.6 to 2.0, more preferably 0.8 to 1.6 blocked or unblocked, isocyanate-reactive groups.

Where appropriate, the polyisocyanate mixtures of the invention, however, may also be admixed in minor amounts to non-functional film-forming binders for the purpose of obtaining very specific properties—for example, as an additive for promoting adhesion.

Any desired substrates are suitable substrates for the coatings formulated using the silane-modified allophanate polyisocyanates of the invention, such as, for example, metal, wood, glass, stone, ceramic materials, concrete, rigid and flexible plastics, textiles, leather and paper, and where appropriate may have been provided with typical primers prior to coating.

Further subjects of this invention are therefore coating compositions comprising the polyisocyanates of the invention, bearing allophanate groups, and also the substrates coated with these coating compositions.

All the references described above are incorporated by reference in their entireties for all useful purposes.

While there is shown and described certain specific structures embodying the invention, it will be manifest to those skilled in the art that various modifications and rearrangements of the parts may be made without departing from the spirit and scope of the underlying inventive concept and that the same is not limited to the particular forms herein shown and described.

EXAMPLES

Unless noted otherwise, all percentages are by weight.

The NCO contents were determined in accordance with DIN EN ISO 11909.

All the viscosity measurements were made with a Physica MCR 51 rheometer from Anton Paar Germany GmbH (Ostfildern) in accordance with DIN EN ISO 3219.

The Hazen colour numbers were determined on a LICO 400 calorimeter from Hach Lange GmbH, Düsseldorf.

The OH numbers stated in the case of the starting compounds A) were calculated from the theoretical molecular weight of the ideal structure (1:1 adduct).

Preparation of the Starting Compounds A)

Hydroxyurethane A1) Containing Silane Groups 221 g (1.0 mol) of 3-aminopropyltriethoxysilane were charged under dry nitrogen to a vessel at room temperature. Added to this initial charge over the course of 15 min, with stirring, were 88 g (1.0 mol) of ethylene carbonate, the mixture warming initially to 34° C. owing to the heat of reaction given off, and the mixture was subsequently stirred at room temperature, without further heating, for 18 hours. An amine titration with 1N HCl showed a conversion of 99.8%.

This gave 2-hydroxyethyl[3-(triethoxysilyl)propyl]urethane as a colourless liquid.

| | |
|---|---|
| Viscosity (23° C.): | 69 mPas |
| OH number (calc.): | 181 mg KOH/g |
| Molecular weight (calc.): | 309 g/mol |

Hydroxyurethane A2) Containing Silane Groups 179 g (1.0 mol) of 3-aminopropyltrimethoxysilane and 88 g (1.0 mol) of ethylene carbonate were reacted with one another by the process described for starting compound A1). The conversion (amine titration with 1N HCl) after 18 hours was 99.6%.

This gave 2-hydroxyethyl[3-trimethoxysilyl)propyl]urethane as a colourless liquid.

| | |
|---|---|
| Viscosity (23° C.): | 245 mPas |
| OH number (calc.): | 210 mg KOH/g |
| Molecular weight (calc.): | 267 g/mol |

Hydroxyurethane A3) Containing Silane Groups 221 g (1.0 mol) of 3-aminopropyltriethoxysilane and 102 g (1.0 mol) of propylene carbonate were reacted with one another by the process described for starting compound A1). The conversion (amine titration with 1N HCl) after 18 hours was 99.9%.

This gave a mixture of 2-hydroxypropyl[3-(triethoxysilyl)propyl]urethane and 2-hydroxy-1-methylethyl[3-(triethoxysilyl)propyl]urethane as a colourless liquid.

| | |
|---|---|
| Viscosity (23° C.): | 86 mPas |
| OH number (calc.): | 173 mg KOH/g |
| Molecular weight (calc.): | 323 g/mol |

Hydroxyurethane A4) Containing Silane Groups 179 g (1.0 mol) of 3-aminopropyltrimethoxysilane and 102 g (1.0 mol) of propylene carbonate were reacted with one another by the process described for starting compound A1). The conversion (amine titration with 1N HCl) after 18 hours was 99.7%.

This gave a mixture of 2-hydroxypropyl[3-(trimethoxysilyl)propyl]urethane and 2-hydroxy-1-methylethyl[3-(trimethoxysilyl)propyl]urethane as a colourless liquid.

| | |
|---|---|
| Viscosity (23° C.): | 326 mPas |
| OH number (calc.): | 199 mg KOH/g |
| Molecular weight (calc.): | 281 g/mol |

Hydroxyamide A5) Containing Silane Groups 221 g (1.0 mol) of 3-aminopropyltriethoxysilane and 86 g (1.0 mol) of γ-butyrolactone were reacted with one another by the process described for starting compound A1). The conversion (amine titration with 1N HCl) after 18 hours was 99.4%.

This gave 4-hydroxy-N-[3-(triethoxysilyl)propyl]butaneamide as a colourless liquid.

| | |
|---|---|
| Viscosity (23° C.): | 326 mPas |
| OH number (calc.): | 199 mg KOH/g |
| Molecular weight (calc.): | 281 g/mol |

Example 1

Inventive 1680 g (10.0 mol) of hexamethylene diisocyanate (HDI) were admixed at a temperature of 80° C. under dry nitrogen with 309 g (1.0 mol) of the hydroxy urethane A1) containing silane groups, and the mixture was stirred for 3 hours until an NCO content of 40.1% was reached, corresponding to complete urethanisation. Subsequently the reaction mixture was heated to 95° C. and 0.5 g of zinc(II) 2-ethyl-1-hexanoate was added as an allophanatization catalyst. The reaction, beginning exothermically, raised the temperature of the mixture to 110° C. After about 30 minutes the NCO content of the reaction mixture was 35.9%. The catalyst was deactivated by addition of 1 g of benzoyl chloride, and the unreacted monomeric HDI was separated off in a thin-film evaporator at a temperature of 130° C. and a pressure of 0.1 mbar. This gave 789 g of a virtually colourless, clear allophanate polyisocyanate having the following characteristics:

| | |
|---|---|
| NCO content: | 13.7% |
| Monomeric HDI: | 0.03% |
| Viscosity (23° C.): | 1270 mPas |
| Colour number (APHA): | 21 Hazen |
| NCO functionality: | >3 (calculated) |
| Silane group content: | 9.6% (calculated as $SiO_3$; mol. weight = 76 g/mol) |

Example 2

Inventive

In accordance with the process described in Example 1, 1680 g (10.0 mol) of HDI were reacted with 267 g (1.0 mol) of the hydroxy urethane A2) containing silane groups. The allophanatization reaction was initiated at an NCO content of 41.0% by addition of 0.5 g of zinc(II) 2-ethyl-1-hexanoate. On reaching an NCO content of 36.7%, the reaction mixture was stopped with 1 g of benzoyl chloride and worked up as described in Example 1. This gave 690 g of a virtually colourless, clear allophanate polyisocyanate having the following characteristics:

| | |
|---|---|
| NCO content: | 14.2% |
| Monomeric HDI: | 0.06% |
| Viscosity (23° C.): | 3050 mPas |
| Colour number (APHA): | 19 Hazen |
| NCO functionality: | >3 (calculated) |
| Silane group content: | 11.0% (calculated as $SiO_3$; mol. weight = 76 g/mol) |

Example 3

Comparative, in Analogy to WO 03/054049

660 g (3.61 eq) of a polyisocyanurate polyisocyanate based on HDI, having an NCO content of 23.0% with an NCO functionality of 3.2, a monomeric HDI content of 0.1% and a viscosity at 23° C. of approximately 1200 mPas were admixed under dry nitrogen at a temperature of 100° C., over the course of 30 minutes, with 340 g (1.45 mol) of N-(n-butyl)-3-aminopropyltrimethoxysilane and the mixture was then stirred for 2 hours until an NCO content of 9.1% was reached, corresponding to complete reaction. This gave a polyisocyanate containing silane groups, in the form of a colourless resin of high viscosity having the following characteristics:

| | |
|---|---|
| NCO content: | 9.1% |
| Monomeric HDI: | 0.03% |
| Viscosity (23° C.): | 183.000 mPas |
| Colour number (APHA): | 37 Hazen |
| NCO functionality: | 1.9 (calculated) |
| Silane group content: | 11.0% (calculated as $SiO_3$; mol. weight = 76 g/mol) |

Example 4

Comparative, in Analogy to WO 02/058569

500 g (2.58 eq) of a polyisocyanurate polyisocyanate based on HDI, having an NCO content of 21.7% with an NCO functionality of 3.5, a monomeric HDI content of 0.1% and a viscosity at 23° C. of approximately 3000 mPas were admixed under dry nitrogen at a temperature of 80° C., over the course of 30 minutes, with 500 g (1.42 mol) of diethyl N-(3-trimethoxysilylpropyl)aspartate, prepared according to Example 5 of EP 0 596 360, and the mixture was then stirred for 2 hours until an NCO content of 4.9% was reached, corresponding to complete reaction. This gave a polyisocyanate containing silane groups, in the form of a colourless resin of high viscosity having the following characteristics:

| | |
|---|---|
| NCO content: | 4.9% |
| Monomeric HDI: | 0.03% |

-continued

| | |
|---|---|
| Viscosity (23° C.): | 127.000 mPas |
| Colour number (APHA): | 65 Hazen |
| NCO functionality: | 1.6 (calculated) |
| Silane group content: | about 10.8% (calculated as SiO$_3$; mol. weight = 76 g/mol) |

The comparative shows that the inventive polyisocyanates containing silane groups, from Examples 1 and 2, combine similar silane group content with a higher isocyanate content, a significantly higher NCO functionality and, in particular, a considerably lower viscosity than the polyisocyanates, containing silane groups, of comparative Examples 3 and 4.

Example 5

Inventive

In accordance with the process described in Example 1, 1680 g (10.0 mol) of HDI were reacted with 323 g (1.0 mol) of the hydroxy urethane A3) containing silane groups. The allophanatization reaction was initiated at an NCO content of 39.8% by addition of 0.5 g of zinc(II) 2-ethyl-1-hexanoate. On reaching an NCO content of 35.6%, the reaction mixture was stopped with 1 g of benzoyl chloride and worked up as described in Example 1. This gave 740 g of a virtually colourless, clear allophanate polyisocyanate having the following characteristics:

| | |
|---|---|
| NCO content: | 13.5% |
| Monomeric HDI: | 0.28% |
| Viscosity (23° C.): | 1680 mPas |
| Colour number (APHA): | 22 Hazen |
| NCO functionality: | >3 (calculated) |
| Silane group content: | 10.3% (calculated as SiO$_3$; mol. weight = 76 g/mol) |

Example 6

Inventive

In accordance with the process described in Example 1, 3360 g (20.0 mol) of HDI were reacted with 281 g (1.0 mol) of the hydroxy urethane A4) containing silane groups. The allophanatization reaction was initiated at an NCO content of 45.0% by addition of 0.5 g of zinc(II) 2-ethyl-1-hexanoate. On reaching an NCO content of 42.7%, the reaction mixture was stopped with 1 g of benzoyl chloride and worked up as described in Example 1. This gave about 705 g of a virtually colourless, clear allophanate polyisocyanate having the following characteristics:

| | |
|---|---|
| NCO content: | 14.6% |
| Monomeric HDI: | 0.21% |
| Viscosity (23° C.): | 2630 mPas |
| Colour number (APHA): | 19 Hazen |
| NCO functionality: | >3 (calculated) |
| Silane group content: | 10.8% (calculated as SiO$_3$; mol. weight = 76 g/mol) |

Example 7

Inventive

In accordance with the process described in Example 1, 1680 g (10.0 mol) of HDI were reacted with 307 g (1.0 mol) of the hydroxy amide A5) containing silane groups. The allophanatization reaction was initiated at an NCO content of 39.8% by addition of 0.5 g of zinc(II) 2-ethyl-1-hexanoate. On reaching an NCO content of 35.6%, the reaction mixture was stopped with 1 g of benzoyl chloride and worked up as described in Example 1. This gave 537 g of a virtually colourless, clear allophanate polyisocyanate having the following characteristics:

| | |
|---|---|
| NCO content: | 12.1% |
| Monomeric HDI: | 0.08% |
| Viscosity (23° C.): | 5270 mPas |
| Colour number (APHA): | 24 Hazen |
| NCO functionality: | 2.0 (calculated) |
| Silane group content: | 14.1% (calculated as SiO$_3$; mol. weight = 76 g/mol) |

Example 8

Inventive

In accordance with the process described in Example 1, 2222 g (10.0 mmol) of 1-isocyanato-3,3,5-trimethyl-5-isocyanatomethylcyclohexane (IPDI) were reacted with 309 g (1.0 mol) of the hydroxy urethane A1) containing silane groups. The allophanatization reaction was initiated at an NCO content of 31.5% by addition of 0.4 g of tin(II) 2-ethyl-1-hexanoate.

On reaching an NCO content of 28.2%, the reaction mixture was stopped with 1 g of benzoyl chloride, and the unreacted monomeric IPDI was separated off in a thin-film evaporator at a temperature of 160° C. and a pressure of 0.1 mbar. This gave 939 g of a viscous, pale yellow allophanate polyisocyanate that after being dissolved in 1-methoxyprop-2-yl acetate, in the form of a 70 percent strength solution, had the following characteristics:

| | |
|---|---|
| NCO content: | 8.4% |
| Monomeric IPDI: | 0.33% |
| Viscosity (23° C.): | 940 mPas (70% in MPA) |
| Colour number (APHA): | 31 Hazen |
| NCO functionality: | >3 (calculated) |
| Silane group content: | about 5.7% (calculated as SiO$_3$; mol. weight = 76 g/mol) |

Example 9

Comparative, in Analogy to EP-A 1273640

500 g (1.39 eq) of a polyisocyanurate polyisocyanate based on IPDI, as a 70 percent strength solution in 1-methoxyprop-2-yl acetate (MPA), having an NCO content of 11.7%, an NCO functionality of 3.3, a monomeric IPDI content of 0.3% and a viscosity at 23° C. of approximately 5010 mPas were diluted with a further 42.9 g of MPA and admixed under dry nitrogen at a temperature of 50° C., over the course of one hour, with 100.0 g (0.23 mol) of bis(3-triethoxysilylpropyl)

amine. Subsequently the mixture was stirred for one hour until an NCO content of 7.5% was reached, corresponding to complete reaction. This gave a pale-coloured polyisocyanate, containing silane groups, in the form of a 70 percent strength solution in 1-methoxyprop-2-yl acetate, which had the following characteristics:

| | |
|---|---|
| NCO content: | 7.5% |
| Monomeric IPDI: | 0.22% |
| Viscosity (23° C.): | 2170 mPas (70% in MPA) |
| Colour number (APHA): | 26 Hazen |
| NCO functionality: | 2.7 (calculated) |
| Silane group content: | about 5.6% (calculated as $SiO_3$; mol. weight = 76 g/mol) |

The comparative shows that the inventive IPDI polyisocyanate containing silane groups, from Example 8, combines a similar silane group content with a higher isocyanate content, a significantly higher NCO functionality and a lower viscosity than the polyisocyanate, containing silane groups, from comparative Example 9.

Example 10

Inventive

In accordance with the process described in Example 1, 2620 g (10.0 mol) of 4,4'-diisocyanatodicyclohexylmethane were reacted with 309 g (1.0 mol) of the hydroxy urethane A1) containing silane groups. The allophanatization reaction was initiated at an NCO content of 37.2% by addition of 0.4 g of tin(II) 2-ethyl-1-hexanoate. On reaching an NCO content of 24.4%, the reaction mixture was stopped with 1 g of benzoyl chloride, and the unreacted monomeric 4,4'-diisocyanatodicyclohexylmethane was separated off in a thin-film evaporator at a temperature of 170° C. and a pressure of 0.1 mbar. This gave 1043 g of a viscous, yellowish allophanate polyisocyanate that after being dissolved in 1-methoxyprop-2-yl acetate, in the form of a 70 percent strength solution, had the following characteristics:

| | |
|---|---|
| NCO content: | 7.2% |
| Monomeric 4,4'-diisocyanato-dicyclohexylmethane: | 0.41% |
| Viscosity (23° C.): | 1145 mPas (70% in MPA) |
| Colour number (APHA): | 37 Hazen |
| NCO functionality: | >3 (calculated) |
| Silane group content: | about 5.1% (calculated as $SiO_3$; mol. weight = 76 g/mol) |

The invention claimed is:

1. A process for preparing polyisocyanates containing allophanate groups comprising reacting
    A) at least one hydroxyurethane and/or hydroxyamide containing silane groups obtained from the reaction of aminosilanes with cyclic carbonates and/or lactones;
    with a molar excess amount, based on the NCO-reactive groups of A), of
    B) at least one diisocyanate having aliphatically, cycloaliphatically, araliphatically, and/or aromatically attached isocyanate groups; and
    optionally subsequently removing unreacted excess diisocyanate.

2. The process of claim 1, wherein A) comprises a reaction product of aminosilanes of general formula (I)

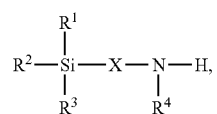

wherein
$R^1$, $R^2$ and $R^3$ are, identically or differently, a saturated or unsaturated, linear or branched, aliphatic or cycloaliphatic, or optionally substituted aromatic or araliphatic radical having up to 18 carbon atoms optionally comprising up to 3 heteroatoms from the series oxygen, sulphur, and nitrogen;

X is a linear or branched organic radical having at least 2 carbon atoms optionally comprising up to 2 imino (—NH—) groups; and $R^4$ is hydrogen, or a saturated or unsaturated, linear or branched, aliphatic or cycloaliphatic, or optionally substituted aromatic or araliphatic radical having up to 18 carbon atoms, or a radical of formula

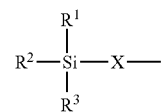

wherein $R^1$, $R^2$, $R^3$, and X are as defined above,
with cyclic carbonates and/or lactones.

3. The process of claim 1, wherein A) comprises a reaction product of aminosilanes of general formula (I)

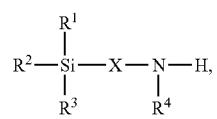

wherein
$R^1$, $R^2$ and $R^3$ are, identically or differently, a saturated, linear or branched, aliphatic or cycloaliphatic radical having up to 6 carbon atoms optionally comprising up to 3 oxygen atoms;

X is a linear or branched alkylene radical having 2 to 10 carbon atoms optionally comprising up to 2 (—NH—) imino groups; and $R^4$ is hydrogen, a saturated, linear or branched, aliphatic or cycloaliphatic radical having up to 6 carbon atoms, or a radical of formula

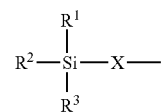

wherein $R^1$, $R^2$, $R^3$, and X are as defined above,
with cyclic carbonates and/or lactones.

4. The process of claim 1, wherein A) comprises a reaction product of aminosilanes of the general formula (I)

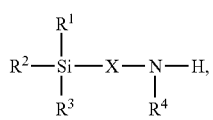

(I)

wherein
R¹, R² and R³ are each alkyl radicals having up to 6 carbon atoms and/or alkoxy radicals which contain up to 3 oxygen atoms, with the proviso that at least one of R¹, R² and R³ is an alkoxy radical;

X is a linear or branched alkylene radical having 3 or 4 carbon atoms; and

R⁴ is hydrogen, a methyl radical, or a radical of the formula

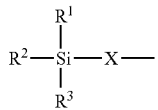

wherein R¹, R², R³, and X are as defined above,
with cyclic carbonates and/or lactones.

5. The process of claim 1, wherein A) comprises a reaction product of aminosilanes of the general formula (I)

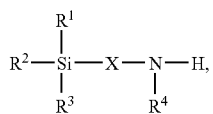

(I)

wherein
R¹, R² and R³ are, identically or differently methyl, methoxy, or ethoxy radical, with the proviso that at least one of R¹, R² and R³ is a methoxy or ethoxy radical;

X is a propylene (—CH₂—CH₂—CH₂—) radical; and

R⁴ is hydrogen, a methyl radical, or a radical of formula

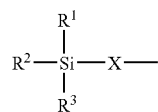

wherein R¹, R², R³, and X are as defined above,
with cyclic carbonates and/or lactones.

6. The process of claim 1, wherein A) comprises reaction products of 3-aminopropyltrimethoxysilane, 3-aminopropyltriethoxysilane, 3-aminopropylmethyldimethoxysilane, and/or 3-aminopropylmethyldiethoxysilane with cyclic carbonates and/or lactones.

7. The process of claim 1, wherein A) comprises reaction products of aminosilanes with ethylene carbonate and/or propylene carbonate.

8. The process of claim 1, wherein A) comprises reaction products of aminosilanes with β-propiolactone, γ-butyrolactone, γ-valerolactone, γ-caprolactone, and/or ε-caprolactone.

9. The process of claim 1, wherein B) comprises diisocyanates having aliphatically and/or cycloaliphatically attached isocyanate groups.

10. The process of claim 1, wherein B) comprises 1,6-diisocyanatohexane, 1-isocyanato-3,3,5-trimethyl-5-isocyanatomethylcyclohexane, 2,4'- and/or 4,4'-diisocyanatodicyclohexylmethane, or mixtures thereof.

11. The process of claim 1, wherein the reaction is carried out in the presence of a catalyst which accelerates the formation of allophanate groups.

12. The process of claim 11, wherein said catalyst comprises zinc carboxylates and/or zirconium carboxylates.

13. The process of claim 11, wherein said catalyst comprises zinc(II) n-octanoate, zinc(II) 2-ethyl-1-hexanoate, zinc (II) stearate, zirconium(IV) n-octanoate, zirconium(IV) 2-ethyl-1-hexanoate, and/or zirconium(IV) neodecanoate.

14. A polyisocyanate containing allophanate groups prepared by the process of claim 1.

15. The polyisocyanate containing allophanate groups of claim 14, wherein said polyisocyanate containing allophanate groups is blocked with blocking agents.

16. A coating composition comprising the polyisocyanate carrying allophanate groups of claim 14.

17. A substrate coated with the coating composition of claim 16.

* * * * *